May 9, 1944. C. FAIRMAN Plant Pat. 627
CHERRY TREE
Filed Sept. 30, 1943
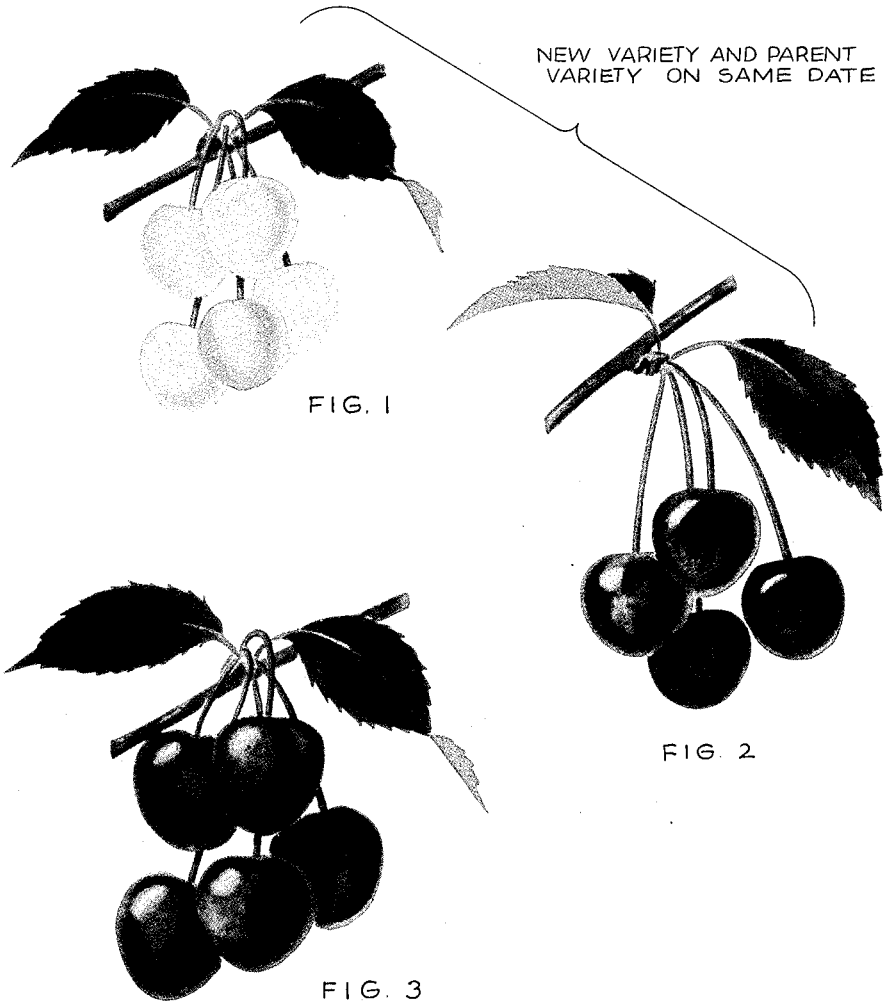
NEW VARIETY TEN DAYS LATER
Inventor
Blanche Fairman
By Robb & Robb
Attorneys Patented May 9, 1944

Plant Pat. 627

UNITED STATES PATENT OFFICE

627

CHERRY TREE

Claude Fairman, near Charlevoix, Mich., assignor to Stark Bro's. Nurseries and Orchards Company, Louisiana, Mo., a corporation of Missouri Application September 30, 1943, Serial No. 504,467

1 Claim. (Cl. 47—62)

The present discovery relates to a new and distinct variety of cherry tree, originating as a bud sport limb on a "Lambert" cherry tree, and found and grown by me in the county of Antrim, State of Michigan.

The "Lambert" cherry is one of the well known hardy types, very dark red in color and of supreme quality for eating and canning purposes.

This new variety differs from its parent in one primary respect, that is, its ripening period which is from ten to fourteen days later when grown under comparable conditions. This characteristic is best shown by the accompanying illustrations in color wherein, Figure 1 shows the ripening condition of the new cherry in comparison with the parent variety at the same date, as illustrated in Figure 2, when mature. In Figure 3 the new variety is illustrated as at maturity about ten days later and in practically all other respects similar to the parent variety, shown in Figure 2.

Asexual reproduction of the sport discloses that this characteristic is fixed.

More specifically, the late ripening habit in relation to that of its parent may be better compared by reference to the respective picking dates for the season of 1943, as follows:

Date of first picking of the sport—July 30th, green.

Date of last picking of the sport—August 10th.

Date of first picking of the parent variety—July 20th.

Date of last picking of the parent variety—July 25th, very ripe.

The following is a detail description of this new variety, so far as is believed necessary, based on observations of specimens grown in Antrim County, Michigan, all color terminology being in accord with general dictionary definitions:

Tree: Medium large; medium vigorous; upright; spreading; hardy; very productive.

*Branches.*—Smooth; dull reddish. *Lenticels*—numerous; small.

*Leaves.*—Length—4¼ inches. Width—2½ inches. Oval to obovate; thin; light to medium green; lightly pubescent. *Margin*—glandular; doubly crenate. *Petiole*—1½ inches long; slender. *Glands*—Average number—none to one to three. Small; globose.

*Flowers.*—Late compared with other varieties. Medium large; white.

Fruit: Maturity when described—overripe, August 10, 1943.

*Size.*—Medium. Axial diameter—⅞ inch. Transverse in suture plane—¾ inch. At right angles to suture plane—⅞ inch.

*Form.*—Roundish-cordate; compressed. *Suture*—an inconspicuous line; shallow. *Cavity*—depth—⅛ inch. breadth—$\frac{3}{16}$ inch.. *Base*—rounded. *Apex*—depressed at center; rounded. *Stem*—length—1¼ inches. Slender; adherent to fruit.

*Skin.*—Thin, adhering to pulp. Color—dark red.

*Flesh.*—Dark red with scant dark red juice. *Texture*—firm; meaty. *Ripens*—fairly even. *Flavor*—sweet; pleasant. *Eating quality*—very good.

*Stone.*—Cling. *Size*—medium. *Length*—$\frac{7}{16}$ inch. Thickness—$\frac{5}{16}$–¼ inch. *Form*—wide ovate. *Sides*—flattened. *Surface*—smooth. *Dorsal edge*—narrow; continuous.

*Use.*—Market; local; dessert; canning.

*Keeping quality.*—Medium good.

*Resistance.*—To insects—medium good. To diseases—medium good.

*Shipping quality.*—Medium good.

I claim:

A new and distinct variety of cherry tree, characterized as to novelty by its late ripening in relation to its parent variety, grown under comparable conditions, substantially as shown and described.

CLAUDE FAIRMAN.